United States Patent
Peclat

[11] Patent Number: 6,102,678
[45] Date of Patent: Aug. 15, 2000

[54] PERISTALTIC PUMP

[75] Inventor: Christian Peclat, Neuchatel, Switzerland

[73] Assignee: Medtronic, Inc., Minneapolis, Minn.

[21] Appl. No.: 09/054,598

[22] Filed: Apr. 3, 1998

[30] Foreign Application Priority Data

Apr. 4, 1997 [CH] Switzerland .................. 97810194

[51] Int. Cl.$^7$ .................................................. F04B 43/08
[52] U.S. Cl. ...................... 417/477.7; 417/474; 417/63; 417/477.1; 417/477.3; 417/477.4; 417/477.6; 604/67; 604/93; 604/253
[58] Field of Search .................. 417/477.8, 63, 417/476, 477.1, 478, 374, 477.3, 477.4, 477.6, 477.7; 604/67, 93, 253

[56] References Cited

U.S. PATENT DOCUMENTS

| | | | |
|---|---|---|---|
| 4,692,147 | 9/1987 | Duggan | 604/93 |
| 4,773,218 | 9/1988 | Wakita et al. | 60/476 |
| 4,820,281 | 4/1989 | Lawler, Jr. | 604/253 |
| 5,083,908 | 1/1992 | Gagnebin et al. | 417/477 |
| 5,205,819 | 4/1993 | Ross et al. | 604/67 |
| 5,322,422 | 6/1994 | Natwick et al. | 417/474 |
| 5,643,207 | 7/1997 | Rise | 604/93 |
| 5,649,808 | 7/1997 | Gruszecki et al. | 417/63 |
| 5,915,932 | 6/1999 | Nabity et al. | 417/477.1 |

FOREIGN PATENT DOCUMENTS

| | | | |
|---|---|---|---|
| 0 026 704 B1 | 4/1986 | European Pat. Off. | F04B 43/12 |
| WO 89/07200 | 10/1989 | WIPO . | |

*Primary Examiner*—Teresa Walberg
*Assistant Examiner*—Leonid Fastovsky
*Attorney, Agent, or Firm*—Curtis D. Kingham; Harold R. Patton

[57] ABSTRACT

The invention is a peristaltic pump having a particularly simple construction and a low axial bulk.

The pump (1) includes a rotor (20) having rollers (21,22,23) which roll against a tube (14) containing the liquid to be pumped. The compression of the tube presses the rollers against the circular peripheral surface (35) of a central vibrating stator (32) in the form of a disc or ring, which guides the rollers and causes them to turn. The stator (32) is set in vibration by piezoelectric means and vibrates by extension in its radial plane following a progressive wave. The chassis (24) of the rotor is devoid of a central drive shaft.

Such a peristaltic pump is notably useful in the medical domain, in machines to be worn by a patient or implanted in the body of a human being or animal.

18 Claims, 4 Drawing Sheets

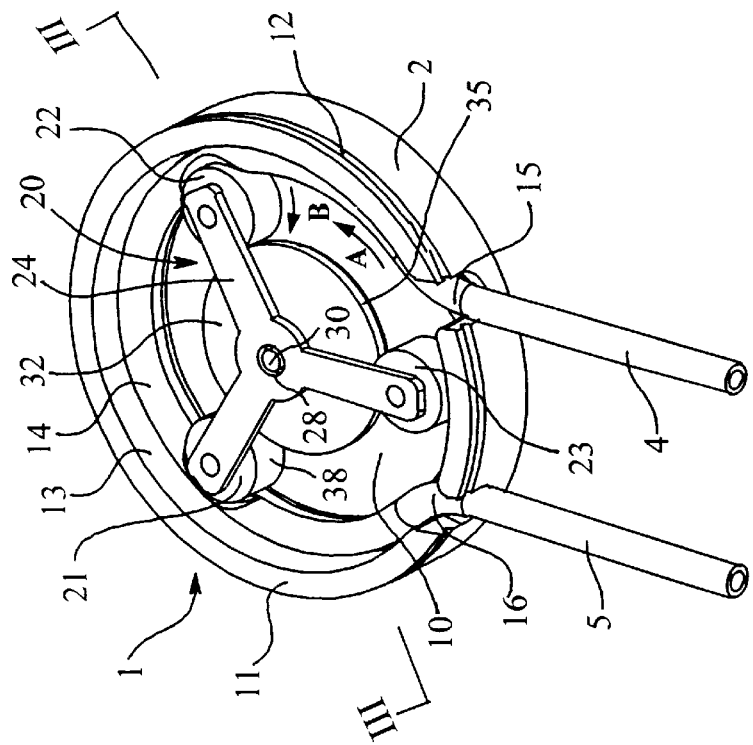
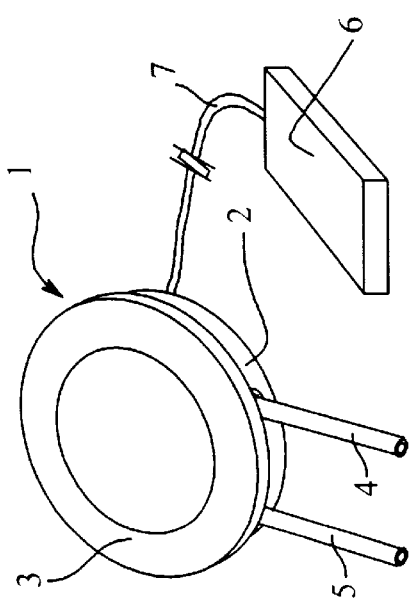
Fig. 1
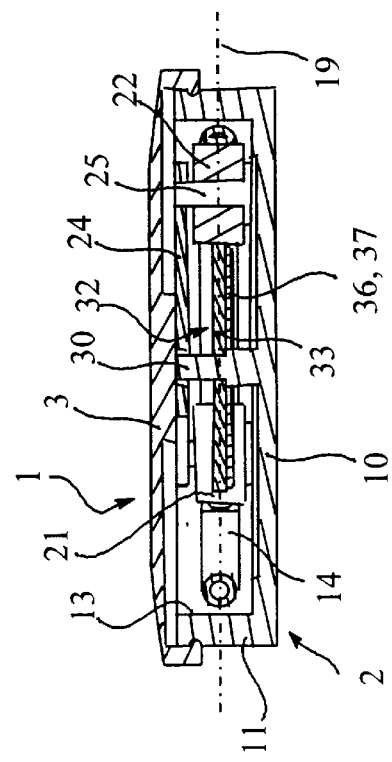
Fig. 2
Fig. 3

PERISTALTIC PUMP

The present invention concerns a peristaltic pump, particularly destined for medical applications, comprising a pump barrel equipped with an interior bearing surface in the form of a circular arc, a rotor, a drive mechanism to turn the rotor and at least one compressible tube holding a liquid to be pumped and arranged in a radial pattern the length of the above mentioned bearing surface. The rotor comprises a rotary chassis fitted with specially designed rollers to roll against the tube, thus compressing it against the bearing surface.

This invention is particularly applicable, but not exclusively, for small portable peristaltic pumps intended for medical uses, in particular for pumps worn externally by a patient or implanted in human beings or in animals to provide precisely measured quantities of a liquid containing hormones, medicaments etc. It is established that such pumps may make use of either a single tube or two tubes connected in parallel and compressed with a matched alternating phase in order that together they supply a more regular output. Two pumps or machines of this kind are described in the patents U.S. Pat. Nos. 4,692,147 and 5,083,908.

These established pumps are generally driven by an electromagnetic motor, normally a step-by-step regulated motor or a continuous current motor linked to a position or outflow sensor, controlled by an electronic control unit which determines the volume of liquid to be ejected in a required period of time. This motor consists of a drive shaft attached to the rotor chassis. Various drawbacks are inherent in such a drive system, the principal one being its cumbersome dimensions. Although all peristaltic pumps, by their very nature, suffer from a certain radial bulk due to the presence of the rollers on the outer edge of the rotor and to the siting of the tube around the rotor, the axial dimensions of the pump itself may be quite small, but to this the volume of the motor has to be added, and this is normally set axially in relation to the pump barrel. Moreover, a reducing-gear is generally necessary to allow the use of a small sized motor and to produce sufficient torque on the rotor shaft. Another drawback is to be found in the fact that electromagnetic motors have a magnetic circuit and may be subject to interference from external magnetic fields, in spite of possible screening precautions. This prevents, for example, the possibility of medical examinations using nuclear magnetic resonance. When these motors are implanted in the body of human beings or animals they need to be free of all lubricant in order to undergo sterilization, otherwise they have to encapsulated without sterilizing them.

The present invention has as its aim a peristaltic pump which allows one substantially to avoid the above drawbacks.

In line with one of the notions that are fundamental to the invention, the drive mechanisms for the pump are of the piezoelectric type. The result is that these drive mechanisms can be produced in a particularly light and compact form with a very small axial volume. Moreover, these drives are practically unaffected by external magnetic influences.

More specifically, the pump's piezoelectric drive system makes advantageous use of a vibrating stator placed between the rollers and having a circular peripheral surface, the vibration of which is effected in parallel on the radial plane in accordance with a progressive wave pattern. This vibration drives the rollers by friction on their circumference.

On the one hand this permits very small dimensions since the stator takes up what is otherwise, in a sense, wasted space, namely the central zone situated between the rollers in the inside of the axial dimensions of the rotor. On the other hand, as the drive is effected on the circumference of the rollers and not on the rotor chassis, there is no need for a drive shaft, nor for reduction-gearing. The pump and its drive system thus utilize very few parts, particularly few moving parts and few bearings. The entire unit can function without lubrication and thus may be sterilized without difficulty.

A particularly advantageous asset of the invention, particularly if the number of rollers is equal to or more than three, is that the rotor does not need to be exactly centered in relationship to the stator, and one can thus dispense with a central bearing. Ideally the rotor chassis is mounted with a radial clearance in relation to the stator, this chassis being placed on the radial plane and driven by the rollers.

Other characteristics and advantages of the present invention will appear in the following description of two preferred production forms and a number of variants, reference being made to the enclosed drawings (appendix), in which:

FIG. 1 is a schematic view, in perspective, of a first production form of a pump as devised by the invention;

FIG. 2 is an enlarged view of the pump in FIG. 1, in perspective, from which the cover has been removed;

FIG. 3 is a schematic view of the pump in cross-section following the line of III—III in FIG. 2;

Figure 5:
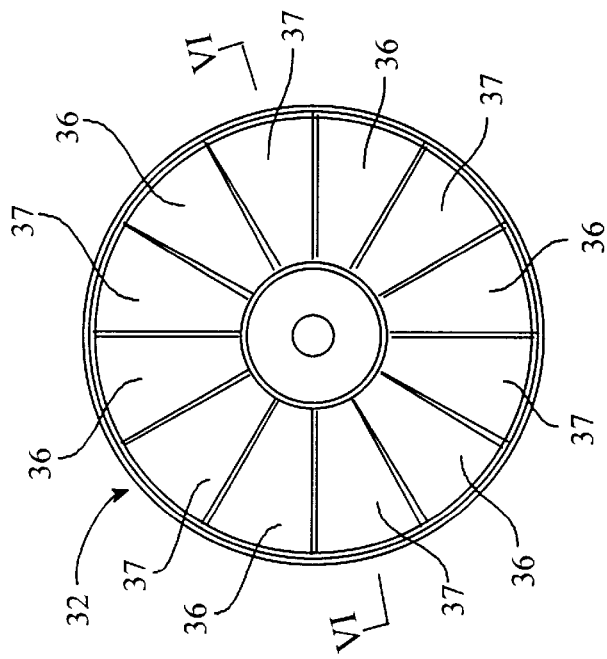
FIG. 5 is a view of the underside of the vibrating stator of the pump in FIGS. 1 to 4.
Figure 6:
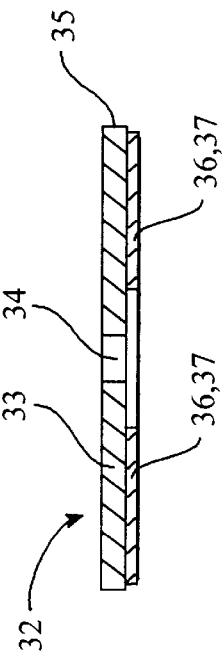
FIG. 6 is a cross-section view following the line VI—VI of FIG. 5.

In FIG. 1 we have given a schematic representation of a peristaltic pump as devised by the invention, comprising a pump barrel 2 of which the upper side is closed by a cover 3. The circuit of the fluid pumped comprises an entry tube 4 and an outlet tube 5 which comes from the barrel 2. We have also represented schematically an electronic control unit for the pump 6, in the form of a separate element 6 connected electrically to the pump by a transmission wire 7, but it is also conceivable that the unit 6 could be housed in the pump housing 2. This unit 6 consists of an electronic control device to control the functioning of the pump 1 on a timed basis, and an electric energy source, for example a battery, to provide current to the device and the drive systems of the pump. As mentioned above, the entire machine as shown in FIG. 1 is ideally intended to be worn by the patient or to be implanted in the body of a human being or an animal. In such an application pump 1 could have a diameter measuring several centimeters, for example approximately 4 cm., and a height in the region of 1 to 2 cm.

FIGS. 2 to 6 represent in greater detail a first production form of the pump 1. The pump barrel 2 has the general shape of a cylindrical bowl of low height and a cylindrical peripheral wall 11. On the external surface of the peripheral wall 11 a groove 12 is cut for the cover 3 to be attached. On the inside, the wall 11 presents a cylindrical support surface 13, the length of which the classic compressible tube 14 of the peristaltic pump is placed. The tube 14 has two bent parts 15 and 16 attached respectively to the entry pipe 4 and outlet pipe 5 and fixed in the openings 17 and 18 (FIG. 4) of the wall 11 of barrel 2. Preferably, parts 4,5,14,15 and 16 should be made as one piece. The tube 14 rests freely against the surface 13 and extends for more than half the interior circumference of barrel 2, preferably over approximately 270°.

In the established manner tube 14 is compressed against the support surface 13 by means of three rotating rollers 21, 22 and 23 which move as indicated by the arrow A, following a circular trajectory around the center of the pump, and rolling against the tube 14 by turning around each other as indicated by arrow B. The displacement following A produces volumetric pumping by displacement of the fluid contained in the tube 14 between two successive rollers. The output of the pump is proportional to the distance traveled by the rollers following arrow A.

Figure 4:
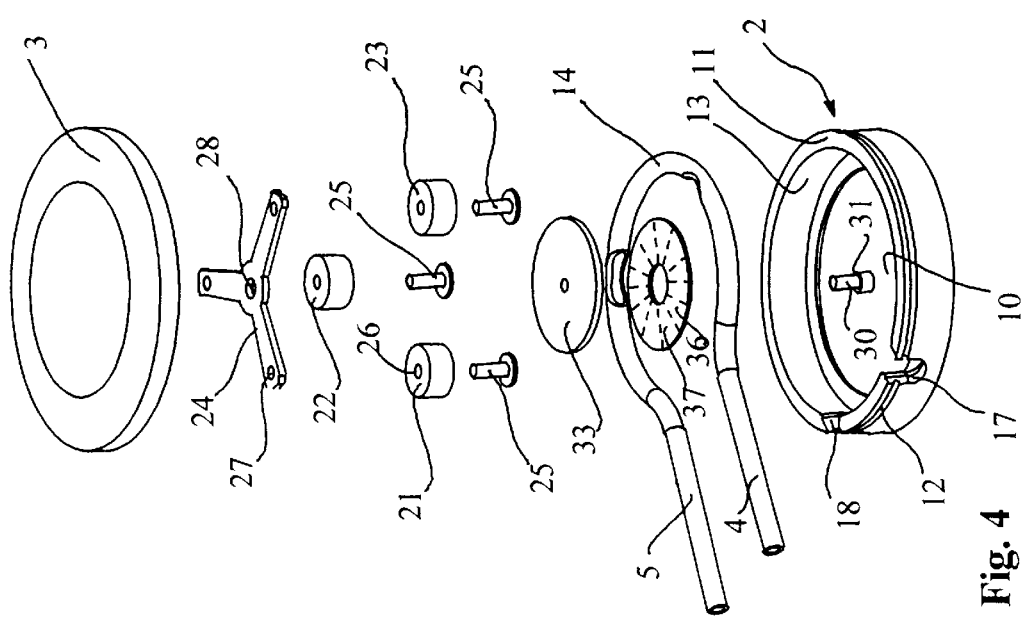
FIG. 4 is an exploded view showing, in perspective, the different components of the pump in FIGS. 1 to 3.

The rollers 21 to 23 are part of a rotor 20 of the pump, comprising a flat rotating chassis 24 having, in this example, the form of a three-pointed star, but it could have any other appropriate shape, such as that of a disc. As is shown in FIG. 4 the roller 21 is mounted in a rotating manner on the extremity of one of the arms of the chassis 24 by means of a pin 25 passing freely through a central hole 26 of the roller 21, this pin being fixed in a corresponding hole 27 of the chassis 24. The two other rollers 22 and 23 are mounted in the same manner on the other arms of the chassis 24. This has a central hole 28.

The barrel 2 also presents on its base 10 a central lug 30 having two successive diameters to form a shouldering 31. The height of the lug 30 is approximately equivalent to that of the wall 11 of the barrel in such a way that the lug passes through the hole 28 and that the cover 3 may rest on the tip of the lug. This lug serves to support a vibrating stator 32 which is connected electrically to the control unit 6 in order to furnish the means for the piezoelectric drive for the pump 1.

As one can see particularly in FIGS. 3 to 6, the vibrating stator 32 consists on the one hand of a resonator 33 in the form of a disc, having a central hole 34 and a circular peripheral surface 35, and on the other hand a series of piezoelectric elements 36, 37 in the form of segments which are all the same size and are stuck against the lower surface of the resonator 33, the elements 37 being arranged alternately with the elements 36. The resonator 33 is fixed to the barrel 2 by chasing the lug 30 to fit into the hole 34 until the resonator rests against the shouldering 31. It then extends on a radial plane 19 preferably to the level of the tube 14.

Ideally each piezoelectric element 36, 37 and 38 is in reality an active zone in the form of a segment of a common ring-shaped plaque of piezoelectric ceramic crystal, for example of the PZT type. The extent of each of these zones is defined by a pair of electrodes connected to the control unit 6 and arranged severally around the plaque in such a way that an electric current applied to the electrodes provokes a deformation of the ceramic plaque on its plane, that is a deformation by extension and contraction in frequency with the alternating electric current. These deformations are transmitted to the resonator 33. The frequency of resonance depends on the shape, the dimensions and the material of the resonator, as well as on the choice of the actual mode of resonance. In practice this frequency is chosen from a range stretching from approximately 20 kHz (audible limit) to approximately 300 kHz. In fact it is only on the lower surface of the ceramic plaque that the electrodes are in the form of segments. On the other surface, the side of resonator 33, there is a single continuous earth electrode in the shape of a disc. The resonator may be connected electrically to the earth electrode or constitute this electrode itself.

All the elements 36 are connected in parallel to receive a first alternating excitation current, whilst all the elements 37 are equally connected in parallel to receive a second alternating excitation current having the same strength and the same frequency as the first, but with a phase displacement of a quarter period. This results in the resonator 33 vibrating by extending in its plane in the shape of a progressive wave which advances around the stator 32 in the opposite direction to that of arrow A in FIG. 2. During this vibration each point on the peripheral surface 35 of the resonator describes an elliptic trajectory in the plane of the resonator which causes a rotation by friction of each roller 21, 22, 23 in the direction of the arrow B. The electrodes and their electrical connections to the control unit 6 are not shown in order to clarify the drawings.

The vibrating elements of this type and their applications for piezoelectric motors, also called ultrasonic motors, are described in particular in an article by Y. Tomikawa, T. Ogasawara and T. Takano entitled "Ultrasonic Motors—Constructions/characteristics/applications", published in Ferroelectrics, 1989, Vol. 91, pp. 163–178 (Gordon and Breach Science Publishers), which is incorporated here by reference.

It must be noted that the vibrating stator 32 could be made simply of a circular piezoelectric ceramic disc or ring, equipped with suitable electrodes on both sides, without the aluminum resonator 33.

In a general manner the progressive wave presents a ventral segment (anti-node) and a pair of nodes for each pair of elements 36 (or 37), that is to say that the stator 32 must comprise at least 4 piezoelectric elements. In order to drive the rollers simultaneously it is preferable that the number of anti-nodes and pairs of nodes be equal to the number of rollers. In the preferred example shown in FIGS. 5 and 6, three pairs of elements 36 and three pairs of elements 37 are foreseen in order to produce a wave having three anti-nodes spaced at 120° to drive the three rollers 21, 22 and 23 simultaneously, which reduces the vibrations in and strains on the rotor.

One will see from the position represented in FIG. 2 that the rollers 21 and 22 are pressed against the tube 14 by pressure against the vibrating stator 32, the circumference 38 of each roller being pressed directly against the peripheral surface 35 of the stator by the elasticity of the material of the tube. Thus these two rollers are guided positively by the stator along a trajectory describing a circular arc. On the other hand the third roller 23 does not roll against tube 14 at that moment, so that it has no tendency to advance even if it is driven in a rotational direction by the stator. It is thus driven in the direction of the arrow A by the rotation of the chasis 24, the position of which in its own plane is determined at every moment by the two rollers 21 and 22 rolling against the tube. The essential function of the chassis 24 is thus solely to maintain the angular distance between the rollers, whilst their trajectory is defined by other means. As a result the rotor 20 does not need to be perfectly centered in relation to the stator, and this is why the central hole 28 of the chassis 24 has a diameter rather larger than that of the lug 30, in order to permit a degree of radial play between the two parts. The rotor 20 therefore does not have a shaft nor a central bearing, the only bearings being formed by the pins 25 which support the rollers. Contrary to the classic peristaltic pumps, the chassis 24 and the pins 25 do not have to transmit any drive torque to the rollers.

The resonator 33 is preferably made of aluminum, but is may also be made of any other material having the appropriate mechanical characteristics, notably regarding its modules of elasticity. The tube 14 is preferably elastomeric. The other parts of the pump may be made of any appropriate material for the intended use, notably of synthetic material to reduce the weight of the pump and the cost of its production. The pump may thus be entirely non-magnetic.

In FIG. 3 one notices that the pump 1 is extremely compact, thanks to the simplicity of its rotor and thanks to the advantageous position of the stator 32 in the space habitually unused inside the trajectory of the rollers, to the extent that the volume of the pump is determined essentially by the dimensions of the rotor.

Figure 7:
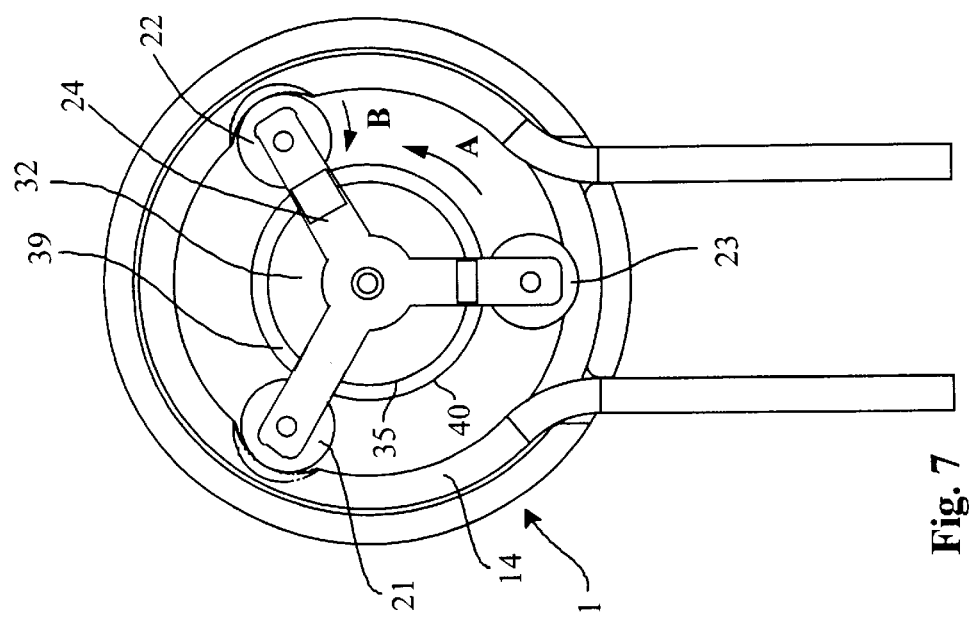
FIG. 7 is an overall view of a variant of the pump shown in FIG. 2.

FIG. 7 represents a variant of the pump 1 described above, where the difference is that the rollers 21, 22 and 23 do not rest directly against the peripheral surface 35 of the stator 32, although they are still driven by means of the progressive wave making this surface vibrate. A rotating ring shaped element 39 surrounds the stator 32, and being pressed against the peripheral surface 35 of the latter by means of elastic (not shown). For example, element 39 may be divided in two or more segments separated at small intervals and pulled towards each other by springs or an elastic band surrounding element 39. A piezoelectric motor of this type is equally described in the publication by Tomikawa et al. cited above.

The ring-shaped element 39 is also pressed against the vibrating stator 32 by the rollers 21 and 22 pushed by the elasticity of the tube 14. The progressive wave drives it in the direction of the arrow A, so that its peripheral surface 40 makes the rollers turn by friction on their circumference. In comparison to the example described above, this construction allows a wider freedom of choice of materials, particularly for that of the rollers since these do not work in direct contact with the vibrating surface. For example, element 39 may comprise a relatively hard basic material for its interior surface resting on the stator 32, and another, less hard, material with a greater coefficient of friction on its outer surface working in contact with the rollers 21 to 23. For the remainder the construction and functioning are the same as in the preceding example.

In a variant one could envisage that the ring shaped element 39 drives each roller by geared transmission, which would avoid all possibility of slippage between them.

Figure 8:
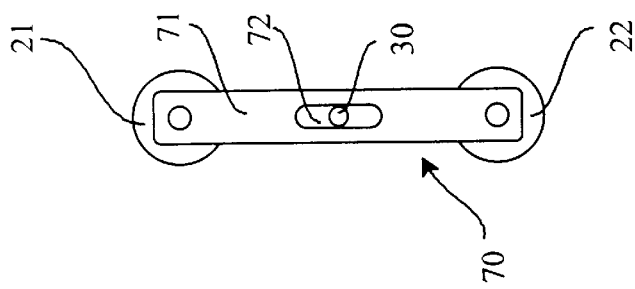
FIG. 8 is a partial view of another variant of the pump shown in FIG. 2.

FIG. 8 shows another variant of the production following FIGS. 1 to 6, where the rotor 20 is replaced by a rotor 70 comprising only two rollers 21 and 22 diametrically opposed to each other. The chassis 71 of the rotor has therefore only two arms diametrically opposed, being laterally guided to drive the roller not touching the tube. For that it has a central hole 72 in the form of a diametrical slot equal in width to the greater diameter of the lug 30 engaged in this hole. This results in a radial play of the rotor in relation to the stator in the direction of the diameter passing through the axes of the two rollers 21 and 22, which allows each roller to follow the trajectory imposed by the periphery of the vibrating stator without creating any substantial stress in the chassis 71. Such a variant with two rollers has the advantage of allowing the use of a resonance mode of a lower level, thus bringing more sizable deformations of the stator and a reduction of the excitation frequency and the number of electrodes. It is also applicable to the other productions described here.

Figure 9:
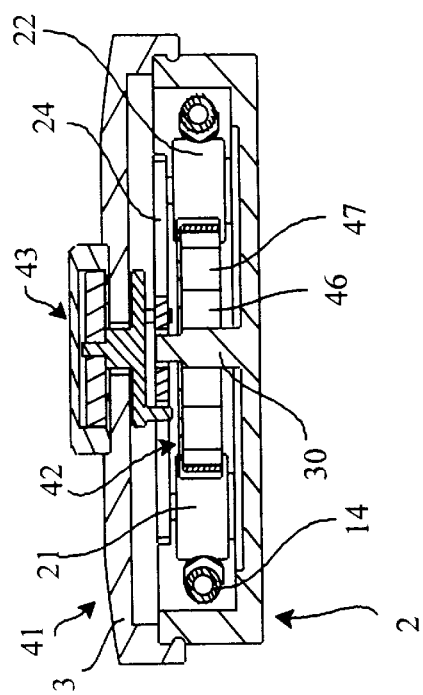
FIG. 9 is a schematic cross section view of a second production form of a pump as devised by the invention.
Figure 11:
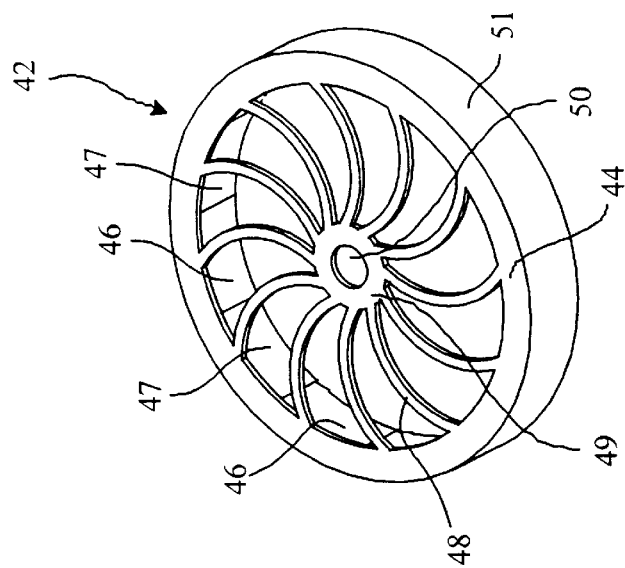
FIG. 11 is a view in perspective of the vibrating stator of the pump in FIG. 9.
Figure 10:
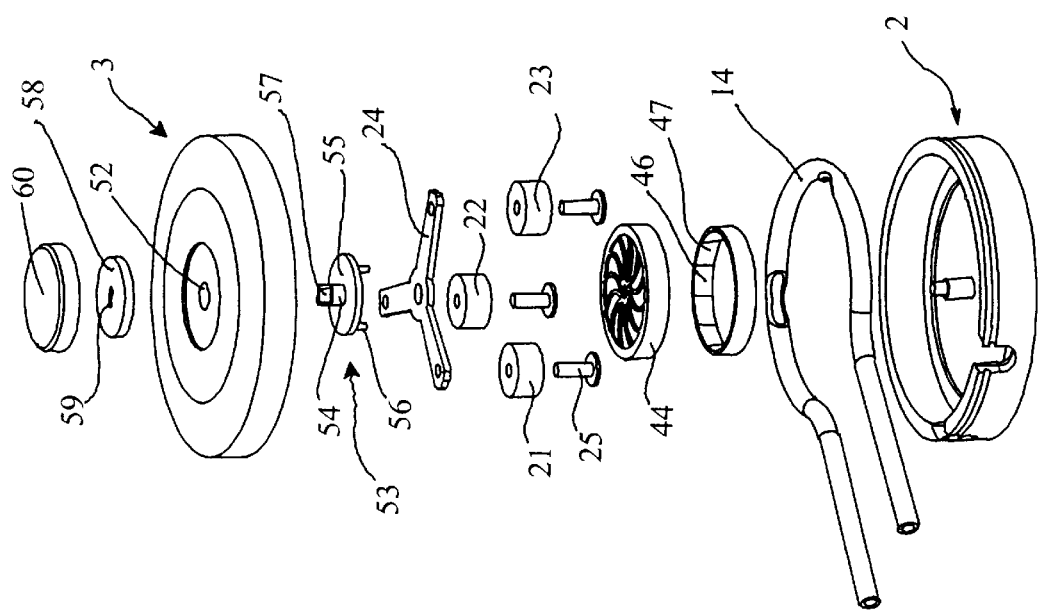
FIG. 10 is an exploded view showing, in perspective, the components of the pump in FIG. 9.

FIGS. 9 to 11 show a second form of production of a peristaltic pump 41 taken from the invention, which is different from the pump 1 described above essentially by virtue of a vibrating stator 42 of a different shape. The pump 41 consists among other things of an angular position sensor 43 which can also be incorporated in the pump 1 and to any other form of production of the invention. The other elements of the pump 41 can be similar to those for pump 1, bearing the same reference numbers, and they will not be described in detail below.

The vibrating stator 42 consists of a resonator formed essentially from a cylindrical vibrating ring 44, and a circular set of piezoelectric elements 46 and 47 arranged alternately on the interior face of the ring 44 and fixed to it to cause its vibration by extension in a radial plane following a progressive wave, following the same principle as described with reference to the vibrating stator 32 of pump 1. The number of elements 46 and 47 can be the same as the elements 36 and 37, and these elements may also each be constituted of an active zone defined by the electrodes on a single piece of piezoelectric ceramic having here a cylindrical shape. To support the vibrating ring 44 the resonator consists of a series of flexible arms 48 perceptibly radial linking this ring to a hub 49 provided with a central hole 50 to be fitted to the central lug 30 of the barrel 2. The ring 44 presents a cylindrical peripheral surface 51 against which the rollers 21 to 23 are pressed by the elasticity of the material of the compressible tube 14. This surface 51 plays the same role as the peripheral surface 35 of the pump 1, but offers a greater surface for contact with the rollers.

Additionally, a specialist in the branch will understand that in comparison with the resonator 33 in the form of a plaque, the resonator 44 in the shape of a ring offers a greater freedom of choice in the dimensions, and thus also in the actual vibration frequencies of the resonator. This might be useful notably to avoid the use of excitation frequencies that are too high when the stator has only a small diameter. Moreover, there is space left in the central region to house the control unit 6, if necessary.

In other respects one will note that the variant of the first form of production, comprising a rotating ring-shaped element 39 as in FIG. 7 is also applicable to the form of production illustrated in the FIGS. 9 to 11.

The angular position sensor 43 is mounted on the cover 3 of the pump barrel above a central boring 52 for the cover. It is linked in rotation to the chassis 24 of the rotor by means of a transmission element 53 having a central hub 54 mounted in rotation in the boring 52. The element 53 comprises a disc 55 placed between the cover 3 and the chassis 24 and provided with clamps 56 which encircle the arms of the chassis 24 so that element 53 turns jointly with the rotor. The hub 54 has a rectangular head 57 designed to drive the rotation sensor.

The sensor 43 may be of any known type, analogue or digital, capable of delivering an electric signal representative of the position of the angular position of the rotor in relation to the cover 3. In this example it is an analogue sensor of the resistor type, comprising an angular resistive encoder in the form of a disc 58 in combination with three terminals which are integral parts of the cover. The rectangular head 57 of the element 53 is engaged in a corresponding slot 59 in the center of the disc 58 to make this turn with the rotor. The disc 58 is retained and guided by a circular cap 60 fastened to the cover 3. The sensor 43 delivers its output signal to the control unit by an electrical connection which is not shown. The control unit may thus measure in real time the volume of liquid ejected by the peristaltic pump.

A specialist will be able to envisage a number of modifications and variants to the examples described above, without leaving the framework of the present invention. In particular one will note that the same principles of construction and drive system are applicable to a peristaltic pump using two tubes in parallel. In such a case the two tubes can be superimposed to be pressed by the same rollers for example if the pressure surface 13 of one of the tubes is displaced in an angular manner in relation to the pressure surface of the other tube, following the principle described in the U.S. Pat. No. 5,083,908 quoted above. These rollers can be driven by a single vibrating stator.

What is claimed is:

1. A peristaltic pump for medical applications, comprising:
    a pump barrel having an interior bearing surface in the form of a circular arc;
    at least one compressible tube capable of holding a liquid to be pumped and arranged in a radial pattern along the length of the bearing surface;
    a rotor comprising a rotary chassis having rollers adapted to roll against the tube, whereby, the tube is compressed against the bearing surface; and, piezoelectric drive means to turn the rotor.

2. The pump of claim 1 wherein the piezoelectric drive means comprises a vibrating stator.

3. The pump of claim 2 wherein the vibrating stator is placed between the rollers.

4. The pump of claim 2 wherein the rollers are pressed against the tube by pressure against the vibrating stator.

5. The pump of claim 2 wherein the vibrating stator has a circular peripheral surface the vibration of which is achieved in accordance with a progressive wave, the vibration driving the rollers.

6. The pump of claim 5 wherein the rollers are pressed against the peripheral surface of the vibrating stator.

7. The pump of claim 5 further comprising a rotating ring-shaped element inserted between the peripheral surface of the vibrating stator and the circumference of each roller whereby, the ring-shaped element is driven by the vibrating stator and drives the rollers on their circumference.

8. The pump of claim 2 wherein the vibrating stator comprises a resonator formed of a vibrating plaque extending along the a radial plane and equipped with piezoelectric elements on at least one of its surfaces.

9. The pump of claim 2 wherein the vibrating stator comprises a resonator formed by a cylindrical vibrating ring equipped with piezoelectric elements on the inner surface.

10. The pump of claim 1 further comprising means for causing the piezoelectric drive means to create a progressive wave.

11. The pump of claim 10 wherein the number of nodes of the progressive wave which are twice as many as the number of rollers.

12. The pump of claim 1 wherein the number of rollers is at least 2.

13. The pump of claim 12 wherein the rollers are diametrically opposed to each other.

14. The pump of claim 1 wherein the number of rollers is at least three.

15. The pump of claim 1 further comprising a means for controlling the piezoelectric drive means.

16. The pump of claim 15 further comprising a position sensor adapted to detect the angular position of the rotating chassis and deliver a corresponding signal to the means for controlling.

17. A peristaltic pump for medical applications, comprising:
    a pump barrel having an interior bearing surface in the form of a circular arc;
    at least one compressible tube capable of holding a liquid to be pumped and arranged in a radial pattern along the length of the bearing surface;
    a rotor comprising a rotary chassis having rollers adapted to roll against the tube, whereby, the tube is compressed against the bearing surface; and,
    piezoelectric drive means to turn the rotor, the piezoelectric drive means comprising a vibrating stator, wherein the rollers are pressed against the tube by pressure against the vibrating stator, the vibrating stator having a circular peripheral surface, the vibration of which is achieved in accordance with a progressive wave, the vibration driving the rollers, wherein the rollers are pressed against the peripheral surface of the vibrating stator.

18. The pump of claim 17 further comprising a position sensor adapted to detect the angular position of the rotating chassis and deliver a corresponding signal to the means for controlling.

* * * * *